United States Patent [19]
Neumaier et al.

[11] 3,988,665
[45] Oct. 26, 1976

[54] EDDY CURRENT TEST COIL ASSEMBLY USING PRINTED CIRCUIT CONDUCTOR MEANS

[75] Inventors: Peter Neumaier; Helmut Reitz, both of Metzingen, Germany

[73] Assignee: Institut Dr. Friedrich Forster, Prufgeratebau, Reutlingen, Germany

[22] Filed: Mar. 12, 1975

[21] Appl. No.: 557,639

[30] Foreign Application Priority Data

May 29, 1974 Germany............................. 2426270

[52] U.S. Cl................................. 324/40; 336/200
[51] Int. Cl.².......................................... G01R 33/12
[58] Field of Search ............... 324/37, 40; 336/200, 336/232

[56] References Cited
UNITED STATES PATENTS

| | | | |
|---|---|---|---|
| 2,542,057 | 2/1951 | Relis | 324/40 |
| 3,135,914 | 2/1964 | Callan et al. | 324/40 |
| 3,281,667 | 10/1966 | Dobbins et al. | 324/40 |
| 3,465,274 | 9/1969 | Proctor | 324/37 |
| 3,504,276 | 3/1970 | Proctor et al. | 324/37 |

FOREIGN PATENTS OR APPLICATIONS
991,890  5/1965  United Kingdom.................. 324/40

OTHER PUBLICATIONS

Moreno, Printed Circuit Coil, IBM Tech. Bull., vol. 12, No. 6, Nov. 1969, p. 778.
O'Donnell, Jr., Flat Circuit Coil, IBM Tech. Bull., vol. 15, No. 2, July 1972, p. 363.
Gonnella et al., Flexible Circuit Solenoid, IBM Tech. Bull., vol. 16, No. 9, Feb. 1974, p. 3008.

*Primary Examiner*—Robert J. Corcoran
*Attorney, Agent, or Firm*—Ervin B. Steinberg; Philip J. Feig

[57] ABSTRACT

An eddy current coil test assembly comprises a printed circuit board having respective conductors which form the excitation coil winding, the sensing coil winding, the input transformer winding, the output transformer winding and the connections between these respective elements. Pot core type transformers are mounted in close proximity to said windings. The printed transformer windings constitute respectively the secondary winding of the input transformer and the primary winding of the output transformer.

2 Claims, 9 Drawing Figures

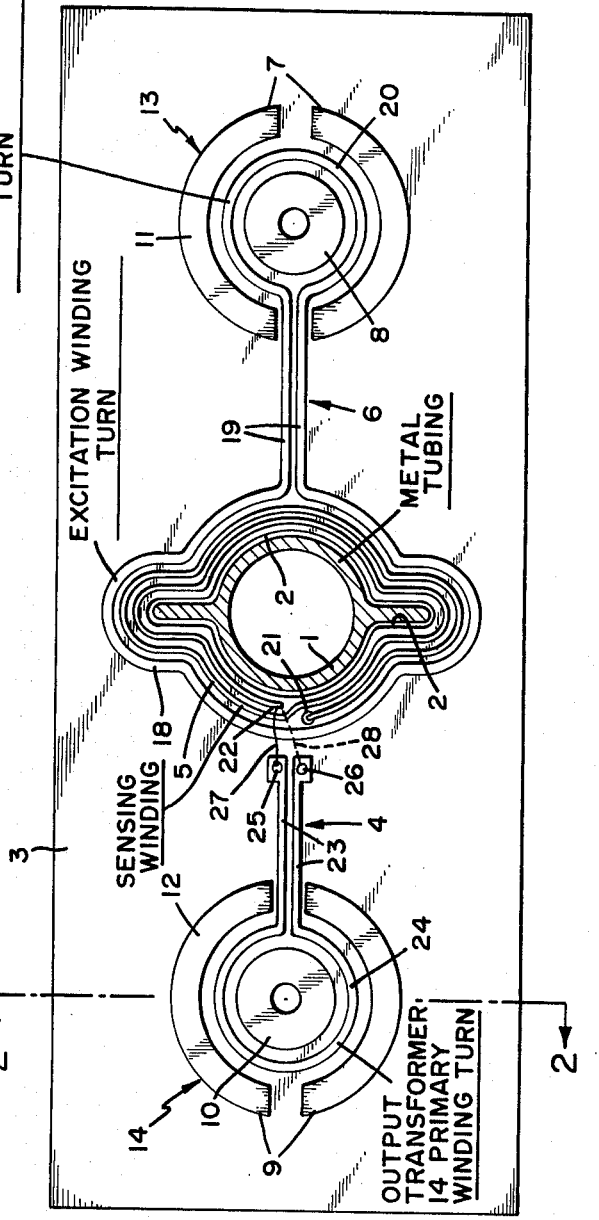
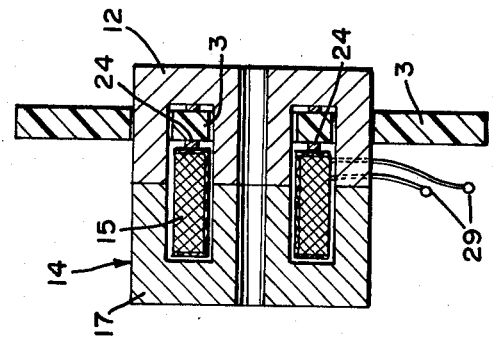
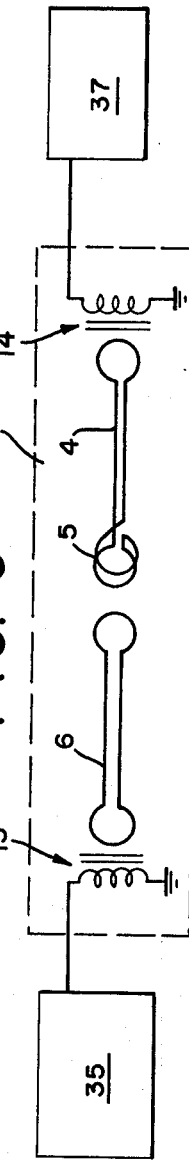

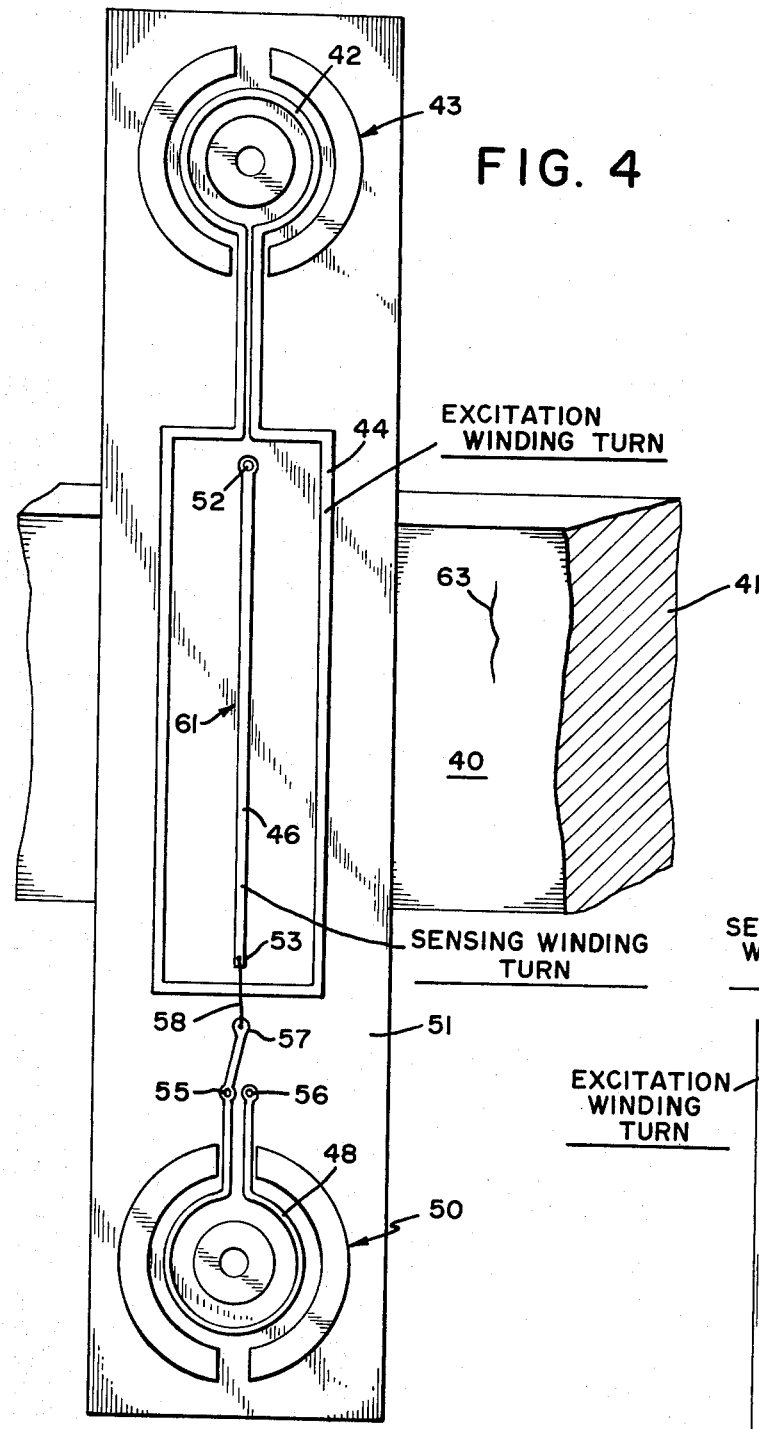
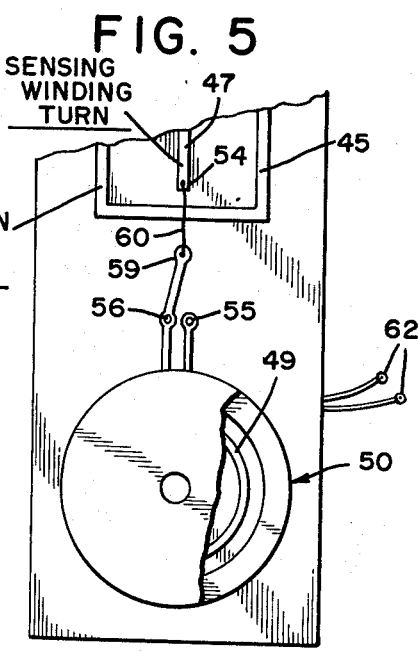

EDDY CURRENT TEST COIL ASSEMBLY USING PRINTED CIRCUIT CONDUCTOR MEANS

BACKGROUND OF THE INVENTION

The present invention concerns an eddy current test coil assembly having at least one excitation winding and at least one sensing winding, each comprising only one or two turns. Eddy current test coils are used to determine the presence of flaws in metal workpieces and to ascertain certain properties of such workpieces.

A test coil assembly of the above type is described, for example, in German patent application DT - OS No. 2,115,247. The coil assembly described therein includes a single turn excitation winding surrounding a tubular workpiecee to be tested and two sensing coils, disposed coaxially on each side of the excitation winding and connected differentially. The advantages which result from the use of single turns are self-evident, namely, simplicity of construction, minimum electrical insulation, low space requirement together with high resolution capability and a short non-tested tube end, made possible because the turns differentially coupled can be disposed in close proximity. There is, however, a further significant advantage. When using eddy current test coils, specifically when small defects are to be located or readings of low amplitude are to be made, it is most important to dispose the sensing winding as close as possible to the surface of the workpiece under test. This is particularly difficult when irregular contours are encountered, e.g. tubes of complex shape. In such a case the test coil winding has to conform to the contour of the workpiece. An arrangement of that type usually is possible only at considerable expense and often can be provided only in an incomplete manner, typically, in the case of surfaces exhibiting indentations. Using single turns, however, it is easy to conform the winding to the surface of any workpiece under test.

Aside from the above stated advantages, the use of single turns for test coils has also significant disadvantages, which to date have prevented this type of coil from being adopted more universally. The high currents required for excitation, lead to contact problems at the plug-in connections of the input cables. The usually low signal amplitude on the sensing portion permits high signal interference from stray fields, particularly those arising in the cable. This, in turn, causes the signal to noise ratio to deteriorate to an unacceptable level. Since it is necessary to match the amplifier input to the low-resistance sensing winding, difficulties also occur on the sensing side resulting from the spontaneous changes in the contact resistance of the plug-in connections. A further aspect concerns the extent to which the differentially coupled turns can be balanced for achieving a minimum residual carrier voltage. With conventional test coils having a large number of turns, it was always easy to effect precise balancing by adding or removing a number of turns on one of the two differential windings. Quite naturally, this physical change cannot be done on single turn coils. In addition, individual turns, according to the patent application referred to above, have to be constructed extremely ruggedly to provide the requisite mechanical strength. This, however, reduces considerably the possibility of measuring eddy current fields immediately above the workpiece surface.

BRIEF SUMMARY OF THE INVENTION

The present invention provides an eddy current test coil assembly of the type indicated which overcomes all or the majority of the disadvantages stated heretofore. More particularly, the present invention discloses a coil arrangement for providing improved signal to noise ratio. In addition, the coil characteristics are easily reproducible from one test coil to another. In the case of differentially coupled windings, the use of precise coil geometry makes the need for residual voltage balancing superfluous. Further, production of the test coil assembly is simpler and less expensive than has been known heretofore.

Specifically, the present invention reveals a test coil assembly in which the turns of the excitation and/or of the sensing windings are provided in the form of printed electrical circuits on a base of insulating material and in which each excitation and/or sensing winding is connected respectively to a secondary winding of an input transformer or to a primary winding of an output transformer, the transformer being located in close proximity to the respective windings.

Printed circuit technology makes it possible to achieve the required high geometrical accuracy at very low cost, provided good reproducibility of coil characteristics and to obtain low residual voltages when using differential connection. It is simple to conform the test coils to the surface or outline of any workpiece under test. The thinness of the wiring comprising the sensing windings, supported by the base, can be located very close to the surface of the workpiece under test, thereby increasing specifically the sensitivity to small defects. All problems related to the low resistance of the single turns are solved by matching transformers which are disposed directly in the test coil assembly. In addition, the test voltage is raised by the output transformer to a level at which the interference from stray fields on long input cables, for all practical purposes, becomes insignificant. The present invention will be described in greater detail hereafter by means of a number of exemplary embodiments.

BRIEF DESCRIPTION OF THE DRAWINGS

FIG. 1 is a plan view of an eddy current test coil assembly in accordance with the present invention;

FIG. 2 is a sectional view along line II—II in FIG. 1;

FIG. 3 is a schematic electrical circuit diagram pertaining to FIGS. 1 and 2;

FIG. 4 is a plan view of an alternative embodiment of an eddy current test coil assembly;

FIG. 5 is a partial view of the underside of the assembly shown in FIG. 4;

DETAILED DESCRIPTION OF THE INVENTION

Figure 6:
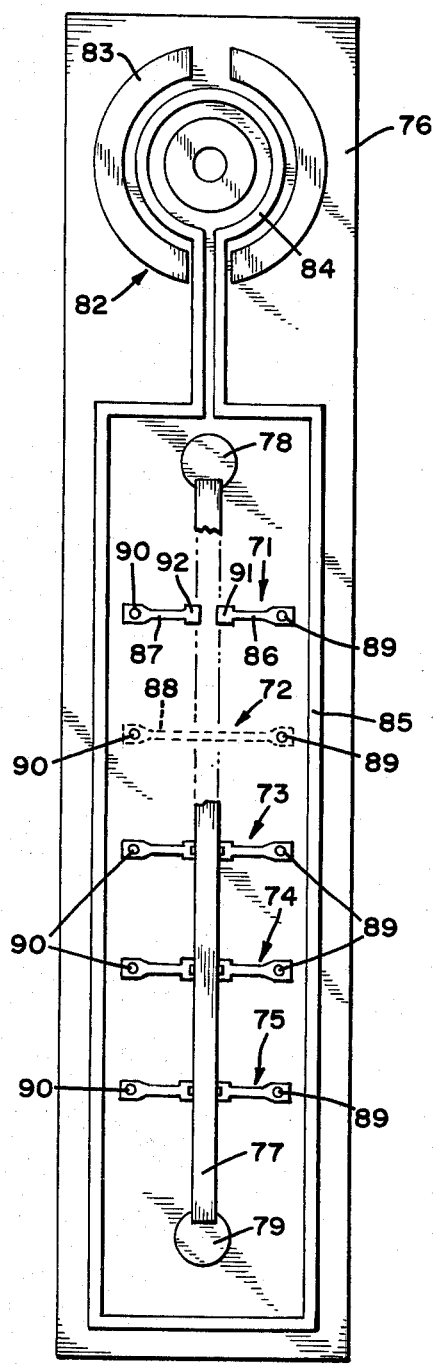
FIG. 6 is a plan view of another eddy current test coil assembly, the assembly having a plurality of sensing windings.

FIGS. 1 and 2 show an eddy current test coil assembly for testing tubular workpieces of various shapes for defects. The workpiece under test, the finned tube 1 shown in section, passes through an aperture 2 disposed in a printed circuit board 3 made of high-grade insulating material, e.g. glass fibre reinforced epoxy resin. The aperture 2 is shaped to fit the contour of the tube 1. The conductors 4, 5 and 6 are bonded to the upper side and underside of the board 3 by one of the standard methods known for fabricating printed circuits, or are provided when the conductive laminate material orginally adhered to the board 3 is etched away. The same circuit pattern is used for the upper side of the board shown in FIG. 1 and the underside of the board, not visible in FIG. 1. Using the high degree of accuracy attainable with the photo-mechanical image transfer method, completely coincident or superposed conductive patterns are produced on the two sides. This will be explained in greater detail below.

Inserted in the apertures 7, 8, 9 and 10 of the board 3 are the lower halves 11 and 12 of the pot cores of the transformers 13 and 14. Both tranformers are identical in construction, and are shown open in FIG. 1. In FIG. 2, which represents a section along the line 2—2, transformer 14 is shown in its entirety, i.e. with a conventionally wound, i.e. wire wound, additional winding 15 and the second half 17 of the pot core. Transformer 13 acts as the input transformer for the excitation winding turn 18 which is formed by the lower portion of the conductor 6. The excitation turn 18 is connected by a parallel pair of conductors 19 to a loop 20, the secondary turn of the transformer 13. On the underside of the printed circuit board 3 and superposed with the conductor 6 runs another conductor. Transformer 13 has a primary winding, not shown here, which is conventionally wound and which in this example should contain about 100 turns. A magnetic flux through the pot core created by the flow of current in the primary winding penetrates the secondary winding 20 and generates a current through the conductor 6 and through which is superposed on it on the underside of the printed circuit board 3 and which cannot be seen in the figure. The two currents together create a magnetic field in an axial plane to the tube 1, which field produces the desired eddy currents in the tube.

Conductor 5 and the conductor coincident with it on the underside of the printed circuit board 3 act as two sensing windings connected differentially, each with two turns, which pick up the changes in the eddy current fields resulting from defects in the material of the tube, convert the sensed changes into voltage signals and conduct the signals to the primary winding of the output transformer 14. The differential circuit is created by means of a plated-through hole 21, through which one end of the conductor 5 on the upper side of the printed circuit board 3 and the corresponding end of the conductor on the underside of the board 3 are connected. The end 22 of the conductor 5 and the end of the superposed conductor on the underside opposite to end 22 serve as connections for the two differentially connected sensing coil turns. Conductor 4, comprising a pair of input conductors 23 and the loop 24, acts as the primary turn of the transformer 14. The conductor 4 via the plated-through holes 25 and 26 is in circuit parallel with the conductor which is coincident with it on the underside of the printed circuit board 3. A length of wire 27 on the upper side connects the end 22 with the hole 25, a length of wire 28 on the underside (shown by dashes) connects the sening winding connection which is opposite to end 22 with the hole 26. In this way, the sensing windings are connected to the primary winding of the transformer 14, which is coupled to the secondary winding 15 comprising, in this example, about 100 turns. Because of the high geometric accuracy of the sensing winding turns, the output voltage appearing at the terminals 29 of the transfomer 14, when providing a defect free workpiece 1, is substantially zero volts even without balancing the windings. If a defect in the workpiece 1 undergoing test passes through the aperture 2, voltage signals of opposing polarity are induced at different times in the sensing windings, and these signals are manifest at the terminals 29, see FIG. 2. The aperture 2 of the coil assembly can be protected against mechanical damage or wear by a small tube of austenitic steel, also suitably contoured for the outline of the tube 1. If, in special cases, it should be necessary to electrically balance the differential assembly, this can be achieved by moving a short-circuit ring of electrically conductive material axially toward one of the two differential windings.

FIG. 3 shows a simplified electrical circuit diagram for the test coil assembly according to FIGS. 1 and 2. The circuit comprises an alternating current generator 35, the test coil assembly 36 and an evaluation unit 37. The latter amplifies, demodulates and evaluates the test responsive output voltage in the normal manner. The assembly 36 includes the transformers 13 and 14 and the conductors 4, 5 and 6 which are connected as described above.

The example described is based on the particularly favorable condition of a common printed circuit board for the test coil windings and the transformer windings. It is possible to use this embodiment with other cases when independent transformers are used. In the example above, two sensing windings are operated differentially connected, but it is possible also to use sensing windings coupled in the absolute value mode.

FIGS. 4 and 5 show another simple test coil assembly, in which, for example, the side 40 of a bar 41 is examined for transverse defects. The electric circuit for this arrangement corresponds largely to that shown in FIG. 3. The two transformers correspond in construction and layout to the transformers 13 and 14 shown in FIGS. 2 and 3. In this case too the secondary turns 42 (second not visible) of the input transformer 43, the excitation winding turns 44, 45 for generating the eddy currents, the sensing coil turn 61 and the primary turns 48, 49 of the output transformer 50 connected to turn 61 are located on the two sides of a printed circuit board 51 made the right way up on both sides by using the same template. The upper side of the board is shown in FIG. 4 and the underside is shown in FIG. 5. The conductors formed by the sensing coil turns 44, 45 and the related secondary turns of the input transformer 43 are superposed upon one another, as are the two conductors 46 and 47. Transformer 43, which as before contains a conventionally wound primary coil, not shown, feeds the excitation turns and generates the eddy currents in the workpiece under test. The conductor 46, a hole 52 plated through with conductive material and the conductor 47 together form the sensing turn 61, the axis of which is perpendicular to the lines of force of the excitation field and whose connections 53, 54 are at the lower ends of the conductors 46 and 47. The two primary turns of the output transformer 50 are connected in parallel via the holes 55 and 56 which are plated through with conductive material. Connection 53 of the sensing coil turn and connection 57 of the transformer 50 is made via a piece of wire 58 and the connection 54 and 59 is made via a piece of wire 60.

When the sensing winding turn 61 is disposed opposite a defect free surface 40 of the workpiece 41, no voltage will be induced in the sensing winding, because of the symmetry of the excitation field and of the eddy reaction field caused thereby. Therefore, no voltage will appear at the output connections 62 of the transformer 50. A disturbance of the reaction field of the eddy currrents, caused for example by a flaw 63, causes a voltage to appear at the output connections 62, the voltage being responsive to the magnitude of the defect. As previously, balancing of the sensing coil output signals becomes superfluous in almost all cases in view of the geometric accuracy which can be achieved with very little effort.

Similarly, coil assemblies matched to irregular surfaces can be produced, for example, by printing circuits on one side of two sheets of thin base material and then adhering the base material to the two sides of a thin intermediate sheet corresponding to the shape of the surface of the workpiece under test. Through connections through the intermediate sheet would need to be made at the locations 52, 55 and 56.

Figure 7:
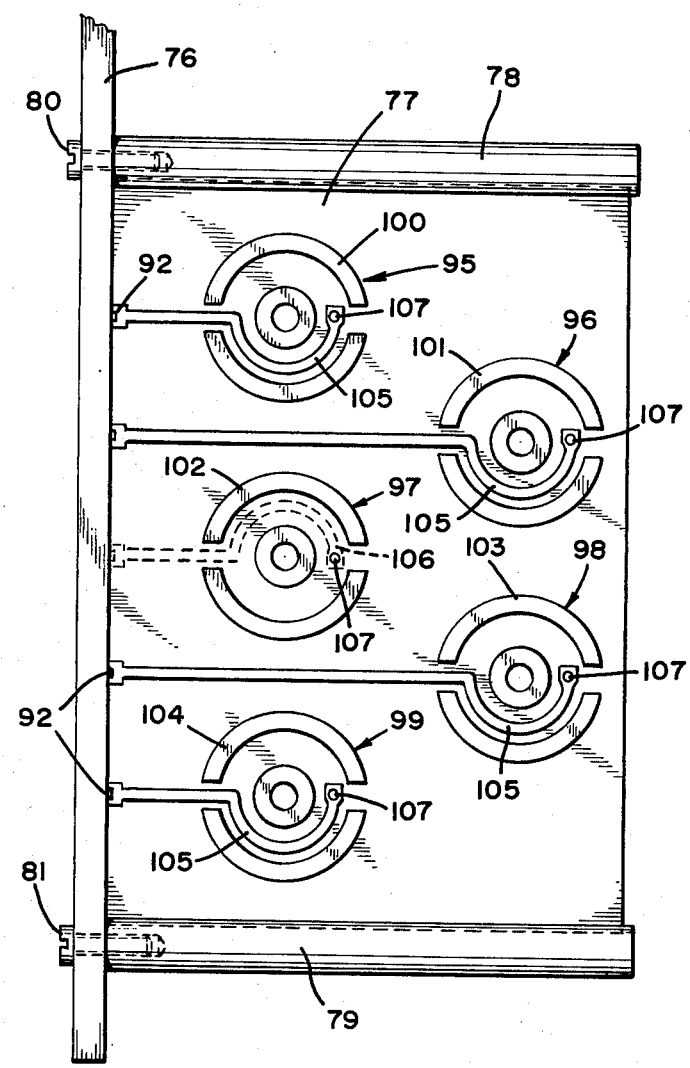
FIG. 7 is a side view of the assembly per FIG. 6.

FIGS. 6 and 7 show a test coil assembly which on the excitation side is identical with the assembly shown in FIGS. 4 and 5, but which has a number, in this example five, separate sensing turns 71 to 75. The assembly comprises two printed circuit boards 76, 77 and two studs 78, 79. The latter are secured to the board 76 by screws 80, 81 and have slots in their sides for holding the board 77. Printed circuit board 76 contains, as described earlier, an input transformer 82 with a pot core 83, a primary winding which is not shown and a secondary winding of which only the turn 84 on the upper side of board 76 is visible. Turn 84 and another coincident with it on the underside of the board feed the excitation winding turn 85 and a corresponding excitation winding turn on the underside. The sensing winding turns 71 to 75 are all identical, and comprise two short conductors 86, 87 on the upper side and a conductor 88 (shown by dashes) opposite them on the underside of the board. The conductors 86, 87 and 88 are connected together through the holes 89, 90, plated through with conductive material, and thus form turns whose axes are perpendicular to the excitation field and whose connection ends are formed at the soldering locations 91, 92. Unlike printed circuit board 76, board 77 can be produced both front and back by the same template. Five transformers 95 to 99 with pot cores 100 to 104 are fitted in the printed circuit board 77 in the manner described above. The primary windings of these transformers are each formed by a half turn 105 on the front of the circuit board and an identical half turn 106 (shown by dashes) on the back, connected together through a hole 107 plated through with conductive material. By means of soldering locations 91, 92 the sensing winding turns are connected to the appropriate output transformers 95 to 99, so that defect responsive signals from the sensing winding turns can be picked up at the output terminals of the secondary windings, not shown, of the transformers. As in the assembly according to FIGS. 4 and 5, the excitation winding turns are geometrically decoupled from the sensing winding turns for as long as the sensing turns are disposed opposite defect-free surfaces of the workpiece.

The advantages of the no-balance sensing coil systems, resulting from the high geometrical accuracy which can be achieved becomes increasingly significant the more sensing coil systems are involved. For example, a large number of sensing winding turns can be installed on a flexible base and distributed around the circumference of a longitudinal item, having, for instance, a hexagonal outline. Making use of the technique described in German patent application No. P 2,326,391 a stationary test system is then capable of providing the high resolution which heretofore has been possible only with rotating scanning heads, each of the sensing coil systems distributed around the circumference being connected, in turn, by an electronic sequencing switch to an evaluation system. This is particularly useful for non-circular outlines, for which it is not possible to use a rotary scanning means of the conventional type.

Figure 8:
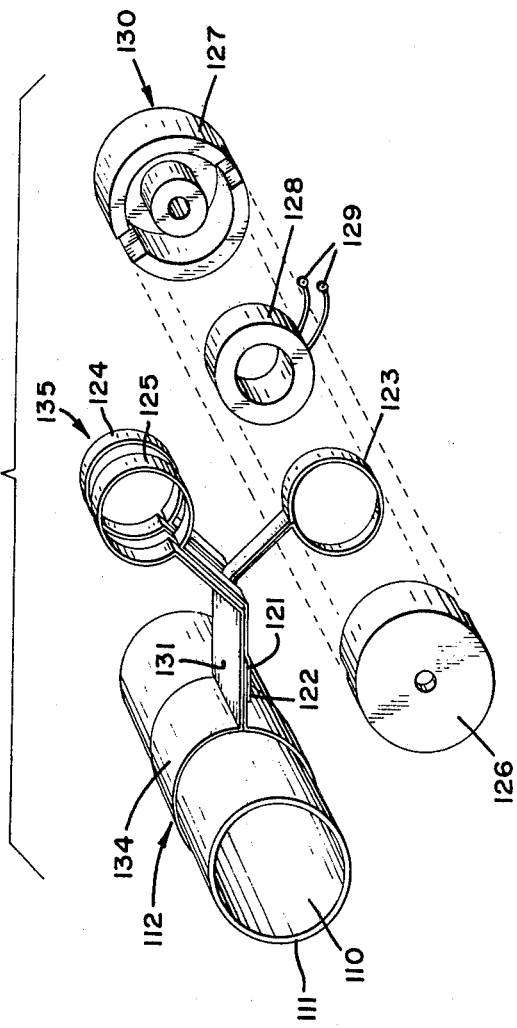
FIG. 8 is a perspective and partially exploded view of another eddy current test coil assembly.
Figure 9:
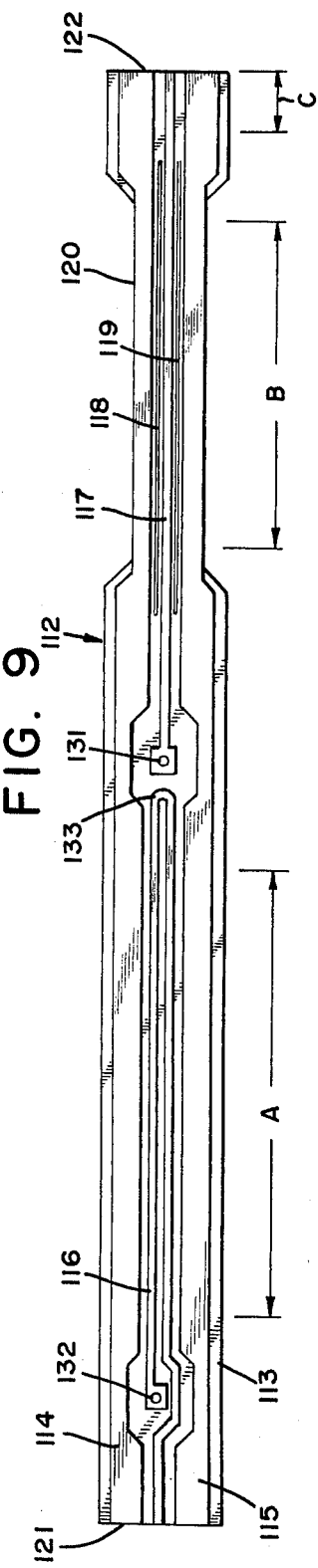
FIG. 9 is a view of the printed circuit board of the assembly shown in FIG. 8, the circuit board being rolled out flat.

FIG. 8 shows a further embodiment of the test coil assembly. This embodiment is used to inspect a longitudinal workpiece which passes through the aperture 110 of a protective tube 111 made of austenitic steel. The circuit used may once again be the same as that shown in FIG. 3. A band 112 encircles the protective tube 111 and one side of band 112 includes a printed circuit. The band is shown in the unrolled state in FIG. 9, and is produced from thin highly flexible base material clad on one side. The base 113, having a reduced portion 120, carries two outer conductors 114 and 115, and two inner conductors 116 and 117. Conductor 116 includes a U-bend 133, and all of the conductors are essentially parallel to each other. Cuts are made in the base 113 along the lines 118 and 119, and the band 112 is then joined along its ends 121 and 122 to form a continuous ring with section C overlapping. The conductors 114, 115 and 116, 117 are individually joined at the overlap, hence providing three continuous conductive loops. Section A of the band 112 is bent around the protective tube 111 to form a loop 134, the end of section A is sharply creased and the loop 134 is adhesively fastened to the protective tube 111. Section B of the inner conductive section, separated along the lines 118, 119, is pulled out downwards, sharp creases are formed at the ends of section B and circular loops 123 and 124, 125 are constructed from the inner and outer conductors within section B. The output transformer 130, shown here in exploded view, includes the pot core halves 126, 127, the secondary winding 128 with terminations 129, and the printed circuit winding loop 123. The input transformer 135 is not shown here for the sake of simplicity, but it is constructed in the same manner as the output transformer, its secondary winding comprising the printed circuit loops 124, 125. The two holes 131 and 132 are in register above one another and are in contact with one another. When all the steps described have been carried out a test coil assembly is derived with two outer excitation winding turns, two sensing winding turns disposed therebetween, connected differentially because of the bend 133, an input transformer 135 is coupled to the excitation turns and an output transformer 130 is coupled to the sensing turns. The mode of operation of the assembly does not differ from that of the assemblies described above.

It can easily be seen that the test coil assembly just described can also be simply matched to the outline of any item under test, for example by making the protective tube 111 of the appropriate shape before attaching the band 112. A number of different versions is possible, for example an absolute coil assembly with one sensing winding only, an assembly with external sensing turns, with the excitation and sensing windings on opposite sides of the base sheet, or with differentially connected excitation turns. In each case high geometrical accuracy is possible, making the assembly easily reproducible. By means of the very thin base sheet it is possible to reduce the clearance between the workpiece under test and the sensing coil winding to a heretofore unattainable minimum.

What is claimed is:

1. An eddy current test coil assembly comprising:
   a base of flexible electrically insulating material;
   an excitation winding in the form of a pair of substantially straight printed conductors disposed on said base;
   a sensing winding in the form of a U-shaped printed conductor disposed on said base;
   a first and a second transformer winding in the form of respective substantially straight printed conductors disposed on said base;
   conductive means in the form of substantially straight conductors disposed on said base and connecting said excitation winding conductors with said first transformer winding conductors;
   all of said conductors, when said base is flat with exception of the base of the U-shaped conductor being substantially parallel to one another and when said base is looped for joining said sensing winding to said second transformer winding being arranged and connected to provide loops for forming an excitation winding loop, a sensing winding loop, and a respective first and a second transformer winding loop.

2. An eddy current test coil assembly as set forth in claim 1, and score lines disposed in said base between said first and said second transformer windings for separating and bending said transformer windings away from each other to provide for each of said transformer windings to become a part of a separate transformer.

* * * * *